(12) United States Patent
Hammerland, III et al.

(10) Patent No.: US 11,771,496 B2
(45) Date of Patent: Oct. 3, 2023

(54) SURGICAL INSTRUMENTS INCORPORATING LIGHT ENERGY TISSUE TREATMENT FUNCTIONALITY

(71) Applicant: Covidien LP, Mansfield, MA (US)

(72) Inventors: John A. Hammerland, III, Arvada, CO (US); William H. Nau, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 224 days.

(21) Appl. No.: 17/308,195

(22) Filed: May 5, 2021

(65) Prior Publication Data
US 2021/0251687 A1 Aug. 19, 2021

Related U.S. Application Data

(63) Continuation of application No. 15/901,009, filed on Feb. 21, 2018, now abandoned.
(Continued)

(51) Int. Cl.
*A61B 18/20* (2006.01)
*A61B 18/18* (2006.01)
*A61B 18/22* (2006.01)
*A61B 18/00* (2006.01)
*A61B 90/00* (2016.01)
*A61B 17/00* (2006.01)

(52) U.S. Cl.
CPC ............ *A61B 18/18* (2013.01); *A61B 18/22* (2013.01); *A61B 2017/00057* (2013.01); *A61B 2018/00035* (2013.01); *A61B 2018/0066* (2013.01); *A61B 2018/00589* (2013.01); *A61B 2018/00595* (2013.01); *A61B 2018/00601* (2013.01); *A61B 2018/00642* (2013.01); *A61B 2018/00708* (2013.01); *A61B 2018/00785* (2013.01); *A61B 2018/00922* (2013.01); *A61B 2018/1807* (2013.01); *A61B 2018/20553* (2017.05); *A61B 2018/2211* (2013.01); *A61B 2018/2266* (2013.01); *A61B 2090/065* (2016.02); *A61B 2218/007* (2013.01)

(58) Field of Classification Search
CPC ..... A61B 18/1807; A61B 18/20; A61B 17/28; A61B 17/29; A61N 5/06
See application file for complete search history.

(56) References Cited

U.S. PATENT DOCUMENTS 4,648,892 A 3/1987 Kittrell et al.
4,695,697 A 9/1987 Kosa
(Continued)

*Primary Examiner* — Lynsey C Eiseman
(74) *Attorney, Agent, or Firm* — Carter, DeLuca & Farrell LLP

(57) ABSTRACT

A tissue-treating portion of a surgical instrument includes a body defining a cavity and a light-energy transmissible sphere captured within the cavity such that a portion of the light-energy transmissible sphere protrudes from the body. The light-energy transmissible sphere is capable of unlimited rotation in all directions relative to the body. The light-energy transmission cable extends through the body to a position spaced-apart from the light-energy transmissible sphere. The light-energy transmission cable is configured to transmit light energy to the light-energy transmissible sphere. The light-energy transmissible sphere, in turn, is configured focus the light energy towards tissue to treat tissue.

7 Claims, 6 Drawing Sheets

Related U.S. Application Data

(60) Provisional application No. 62/471,108, filed on Mar. 14, 2017.

(56) References Cited

U.S. PATENT DOCUMENTS

| | | | |
|---|---|---|---|
| 5,041,109 A | 8/1991 | Abela | |
| 5,359,685 A | 10/1994 | Waynant et al. | |
| 5,361,316 A | 11/1994 | Tanaka et al. | |
| 5,383,901 A | 1/1995 | McGregor et al. | |
| 5,738,677 A | 4/1998 | Colvard et al. | |
| 5,782,825 A | 7/1998 | Anderson | |
| 5,784,508 A | 7/1998 | Turner | |
| 5,968,033 A | 10/1999 | Fuller et al. | |
| 5,980,504 A | 11/1999 | Sharkey | |
| 6,015,404 A | 1/2000 | Altshuler et al. | |
| 6,063,081 A | 5/2000 | Mulier et al. | |
| 6,103,339 A | 8/2000 | Lin | |
| 6,174,307 B1 | 1/2001 | Daniel et al. | |
| 6,358,248 B1 | 3/2002 | Mulier et al. | |
| 6,522,827 B1 | 2/2003 | Loeb et al. | |
| 2002/0128648 A1 | 9/2002 | Weber et al. | |
| 2003/0023236 A1 | 1/2003 | Gowda et al. | |
| 2007/0282404 A1 | 12/2007 | Cottrell et al. | |
| 2013/0102843 A1* | 4/2013 | Feuer | A61B 17/3417 600/114 |
| 2016/0157928 A1* | 6/2016 | Eshkol | G02B 6/14 385/32 |
| 2016/0346034 A1* | 12/2016 | Arya | A61B 18/22 |

\* cited by examiner

SURGICAL INSTRUMENTS INCORPORATING LIGHT ENERGY TISSUE TREATMENT FUNCTIONALITY

CROSS REFERENCE TO RELATED APPLICATION

The present application claims priority to U.S. patent application Ser. No. 15/901,009, filed on Feb. 21, 2018, which claims the benefit of and priority to U.S. Provisional Application Ser. No. 62/471,108, filed on Mar. 14, 2017. The entire contents of each of the foregoing applications are incorporated herein by reference.

BACKGROUND

1. Technical Field

The present disclosure relates generally to the field of surgical instruments. In particular, the present disclosure relates to surgical instruments configured for treating tissue with light energy and multi-function surgical instruments incorporating light energy tissue treatment functionality.

2. Background of Related Art

Energy-based surgical instruments are widely used by surgeons to treat various different tissues in various different manners. These energy-based surgical instruments utilize various different forms of energy such as, for example, RF energy, ultrasonic energy, microwave energy, thermal energy, light energy, etc., and are capable of achieving various tissue effects such as, for example, energy-based dissection, coagulation, cauterization, sealing, etc.

Energy-based surgical pencils, for example, may be utilized to dissect through tissue and/or along the surface of tissue, to cauterize tissue, to spot coagulate tissue, or for other purposes. Such energy-based surgical pencils may be stand-alone devices, or may be incorporated into multi-function devices. When used in conjunction with energy-based surgical forceps, for example, the energy-based surgical pencils may be utilized to provide access to target tissue and/or to treat surrounding tissue. The surgical forceps may then be utilized to treat the target tissue, utilizing both mechanical clamping action and energy to effect hemostasis by heating the target tissue to treat, e.g., coagulate, cauterize, and/or seal, the target tissue. Energy-based surgical pencils may likewise be used in conjunction with other surgical instruments (whether stand-alone or incorporated therein), such as other energy-based instruments, surgical clip appliers, surgical staplers, mechanical graspers, etc.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a tissue-treating portion of a surgical instrument. The tissue-treating portion includes a body defining a cavity and a light-energy transmissible sphere captured within the cavity such that a portion of the light-energy transmissible sphere protrudes from the body. The light-energy transmissible sphere is capable of unlimited rotation in all directions relative to the body. A light-energy transmission cable extends through the body to a position spaced-apart from the light-energy transmissible sphere. The light-energy transmission cable is configured to transmit light energy to the light-energy transmissible sphere. The light-energy transmissible sphere, in turn, is configured to focus the light energy towards tissue to treat tissue.

In an aspect of the present disclosure, the cavity of the body includes a pocket and a distal mouth in communication with the pocket. The light-energy transmissible sphere defines a diameter greater than a diameter of the distal mouth and less than a diameter of the pocket such that the light-energy transmissible sphere is captured within the pocket with a portion of the light-energy transmissible sphere extending through the distal mouth to protrude from a distal end portion of the body.

In another aspect of the present disclosure, the light-energy transmission cable extends to a position proximally spaced-apart from the light-energy transmissible sphere.

In yet another aspect of the present disclosure, a second light-energy transmission cable is configured to transmit light energy to the light-energy transmissible sphere to treat tissue. Alternatively or additionally, one or more second light-energy transmission cables are configured to pass light through the light-energy transmissible sphere for reflection from tissue to enable the detection of at least one property of tissue and/or to detect at least one property of tissue by receiving light energy reflected from tissue.

In still another aspect of the present disclosure, a fluid-delivery lumen is disposed in communication with the cavity. The fluid-delivery lumen is configured to deliver fluid to the cavity in the body. In embodiments, the fluid suspends the light-energy transmissible sphere within the body, and flows out of the body into a surgical site. Further, a suction lumen may be operably associated with the body and configured to permit withdrawal of the fluid from the surgical site.

In still yet another aspect of the present disclosure, a pressure sensor is disposed within the cavity. The one pressure sensor is configured to sense a pressure of the sphere against an interior surface of the body that defines the cavity.

A surgical instrument provided in accordance with aspects of the present disclosure includes a shaft defining a distal end portion, a cavity defined within the distal end portion of the shaft and including a pocket and a distal mouth in communication with the pocket, a light-energy transmissible sphere disposed within the cavity, and a light-energy transmission cable extending through the shaft to a position proximally spaced-apart from the light-energy transmissible sphere. The light-energy transmissible sphere defines a diameter greater than a diameter of the distal mouth and less than a diameter of the pocket such that the light-energy transmissible sphere is captured within the pocket with a portion of the light-energy transmissible sphere extending through the distal mouth to protrude from the distal end portion of the shaft. The light-energy transmissible sphere is capable of unlimited rotation in all directions relative to the distal end portion of the shaft. The light-energy transmission cable is configured to transmit light energy to the light-energy transmissible sphere, while the light-energy transmissible sphere is configured to focus the light energy towards tissue to treat tissue.

In an aspect of the present disclosure, a second light-energy transmission cable is configured to transmit light energy to the light-energy transmissible sphere to treat tissue. Alternatively or additionally, one or more second light-energy transmission cables are configured to pass light through the light-energy transmissible sphere for reflection from tissue to enable the detection at least one property of tissue and/or to detect at least one property of tissue by receiving light energy reflected from tissue.

In another aspect of the present disclosure, a fluid-delivery lumen extends through the shaft and is disposed in communication with the cavity. The fluid-delivery lumen is configured to deliver fluid to the cavity in the body. In embodiments, the fluid suspends the light-energy transmissible sphere within the body, and flows out of the body into a surgical site. Further, a suction lumen may be operably associated with the shaft and configured to permit withdrawal of the fluid from the surgical site.

In still another aspect of the present disclosure, a pressure sensor is disposed within the cavity. The pressure sensor is configured to sense a pressure of the sphere against an interior surface of the distal end portion of the shaft that defines the cavity.

In yet another aspect of the present disclosure, the surgical instrument further includes a handle. The shaft is coupled to and extends distally from the handle. The handle includes an activation switch selectively activatable to supply light energy to the light-energy transmissible sphere.

Another surgical instrument provided in accordance with aspects of the present disclosure includes a shaft and an end effector assembly extending distally from the shaft. The end effector assembly includes first and second jaw members, at least one of which is movable relative to the other between a spaced-apart position and an approximated position. One or both of the jaw members is adapted to connect to a source of energy for treating tissue grasped between the jaw members. A body is operably associated with one of the first or second jaw members, the body defines a cavity including a pocket and a distal mouth in communication with the pocket. A light-energy transmissible sphere is disposed within the cavity. The light-energy transmissible sphere defines a diameter greater than a diameter of the distal mouth and less than a diameter of the pocket such that the light-energy transmissible sphere is captured within the pocket with a portion of the light-energy transmissible sphere extending through the distal mouth to protrude distally from the body. The light-energy transmissible sphere is capable of unlimited rotation in all directions relative to the body. A light-energy transmission cable extends through the shaft to a position proximally spaced-apart from the light-energy transmissible sphere. The light-energy transmission cable is configured to transmit light energy to the light-energy transmissible sphere which, in turn, is configured to focus the light energy towards tissue to treat tissue.

In an aspect of the present disclosure, the light-energy transmissible sphere is aligned with a longitudinal axis of the end effector assembly at least when the first and second jaw members are disposed in the approximated position.

In another aspect of the present disclosure, a second light-energy transmission cable is configured to transmit light energy to the light-energy transmissible sphere to treat tissue. Alternatively or additionally, one or more second light-energy transmission cables are configured to pass light through the light-energy transmissible sphere for reflection from tissue to enable the detection at least one property of tissue and/or to detect at least one property of tissue by receiving light energy reflected from tissue.

In yet another aspect of the present disclosure, a fluid-delivery lumen extends through the one of the first or second jaw members and is disposed in communication with the cavity. The fluid-delivery lumen is configured to deliver fluid to the cavity in the body. In embodiments, the fluid suspends the light-energy transmissible sphere within the body, and flows out of the body into a surgical site. Further, a suction lumen may be operably associated with the end effector assembly and configured to permit withdrawal of the fluid from the surgical site.

In still another aspect of the present disclosure, a pressure sensor is disposed within the cavity. The pressure sensor is configured to sense a pressure of the sphere against an interior surface of the body that defines the cavity.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 3:
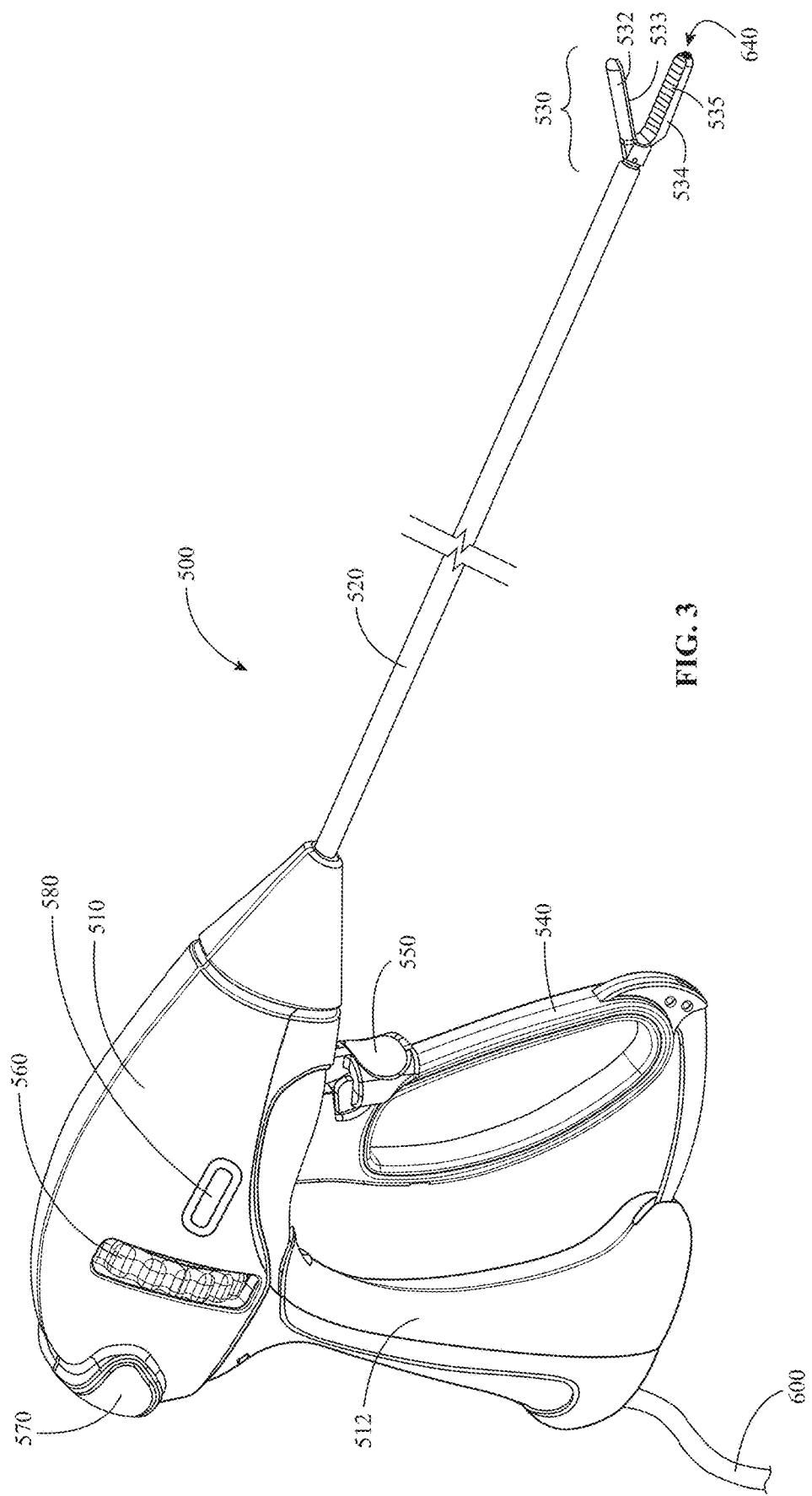
FIG. 3 is a perspective view of a multi-function surgical instrument provided in accordance with the present disclosure.

The present disclosure relates to surgical instruments configured for treating tissue with light energy, e.g., surgical pencil 100 (FIG. 1), and multi-function surgical instruments incorporating light energy tissue treatment functionality, e.g., surgical forceps 500 (FIG. 3). However, although the aspects and features of the present disclosure are detailed hereinbelow with respect to surgical pencil 100 (FIG. 1) and surgical forceps 500 (FIG. 3), the aspects and features of the present disclosure are equally applicable for use with other suitable surgical instrument configurations, whether stand-alone light energy tissue treatment instruments or multi-function surgical instruments incorporating light energy tissue treatment functionality. Although different mechanical and electrical considerations apply to each particular configuration of surgical instrument; however, the aspects and features of the present disclosure with respect to light energy tissue treatment remain generally consistent regardless of the particular configuration of surgical instrument used.

Figure 1:
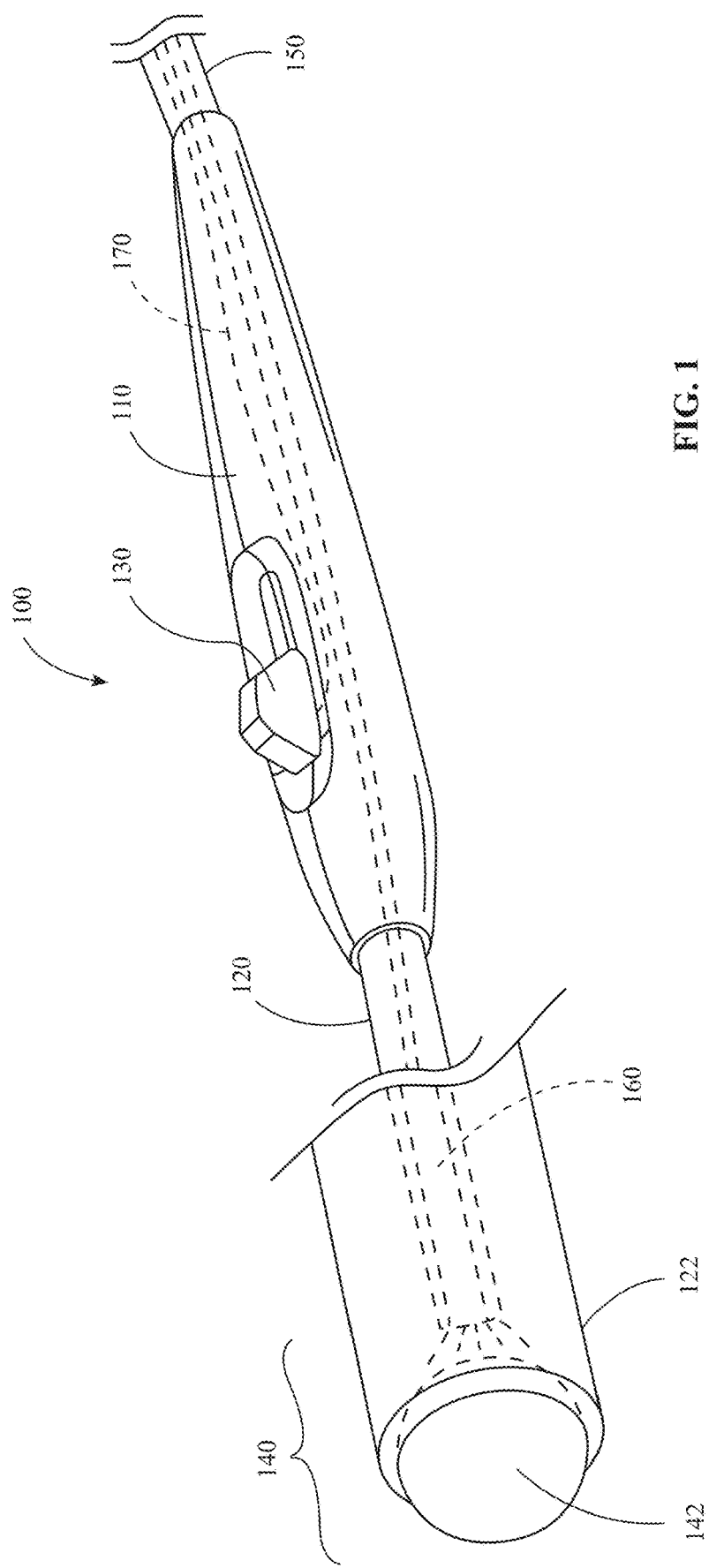
FIG. 1 is a perspective view of a surgical pencil provided in accordance with the present disclosure wherein a distal end portion of the surgical pencil is enlarged to better illustrate the features thereof.

Turning to FIG. 1, surgical pencil 100 generally includes a handle 110, a shaft 120 extending distally from handle 110, one or more activation switches 130 operably disposed on handle 110, and a tissue-treating portion 140 supported on a distal end portion 122 of shaft 120. Surgical pencil 100 may be coupled to a light energy surgical generator (not shown) or other suitable light energy source via a cord 150 or, alternatively, may be configured as a cordless device incorporating portable power and light energy generating components (not shown) on or within handle 110. More specifically, light energy transmission cable(s) 160, e.g., fiber optic cable(s), and/or control wire(s) 170, e.g., electrical wires, are configured to extend through cord 150 and surgical pencil 100 to interconnect the light energy surgical generator (not shown), activation switch 130, and tissue-treating portion 140 with one another to enable the selective supply of light energy to tissue-treating portion 140 for treating tissue upon activation of activation switch 130. Activation switch 130 may be a slide-switch (as shown) or may be configured as a push button switch, rocker switch, etc. Further, activation switch 130 may be configured as an ON/OFF switch, a progressive switch, a discrete multi-position switch, or may include multiple switches. Progressive and discrete multi-position switches, and configurations where multiple switches are provided, enable the selective supply of light energy to tissue-treating portion 140 at different intensity settings, e.g., low and high power, and/or with different energy characteristics, e.g., wavelengths, to provide different tissue treatment effects, e.g., dissection, cauterization, coagulation, blends thereof, etc. Control wire(s) 170 communicate the position of the activation switch(es) 130 to light energy surgical generator (not shown) such that an appropriate light energy is transmitted therefrom to tissue-treating portion 140.

Figure 2A:
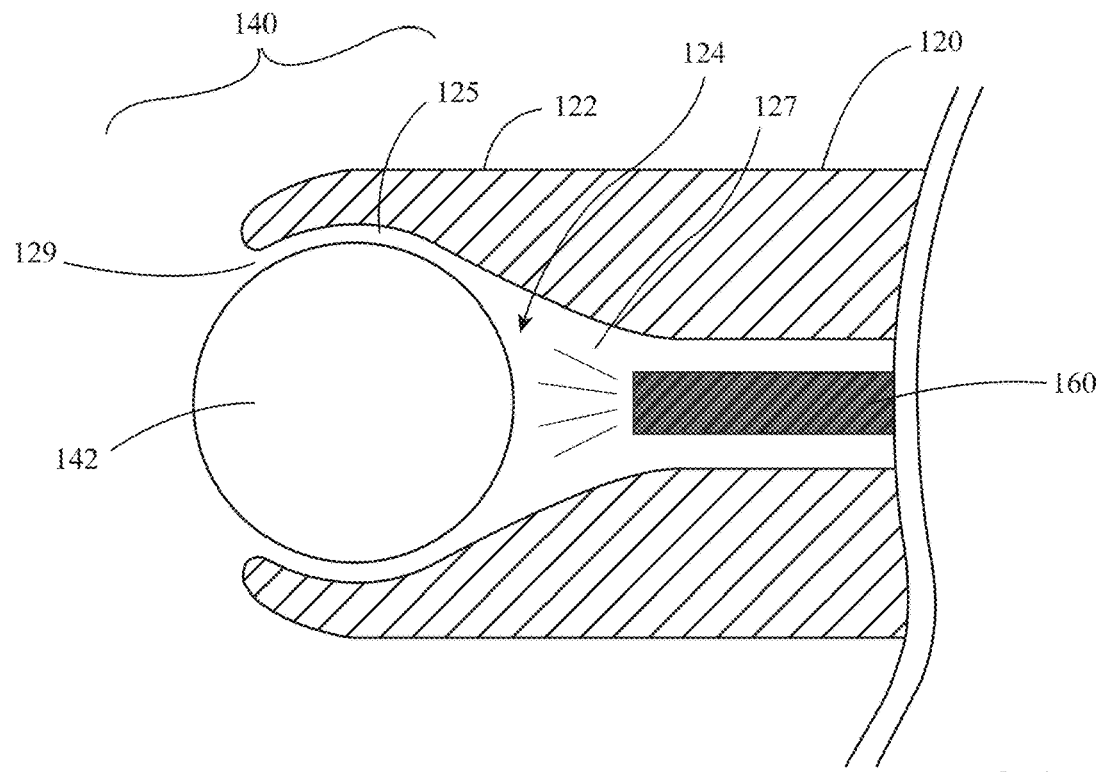
FIG. 2A is an enlarged, longitudinal, cross-sectional view of the distal end portion of the surgical pencil of FIG. 1.

With additional reference to FIG. 2A, tissue-treating portion 140, as mentioned above, is supported on a distal end portion 122 of shaft 120, which serves as the body of tissue-treating portion 140. Tissue-treating portion 140 includes a sphere 142 captured within distal end portion 122 of shaft 120 such that a portion of sphere 142 protrudes distally from distal end portion 122 of shaft 120 and such that sphere 142 is capable of unlimited rotation in any direction relative to shaft 120. To achieve this configuration, sphere 142 is disposed within a cavity 124 defined within distal end portion 122 of shaft 120. Cavity 124 includes a pocket 125 defining a diameter greater than that of sphere 142, a proximal throat 127 communicating with pocket 125 and defining a diameter less than that of sphere 142, and a distal mouth 129 communicating with pocket 125 and defining a diameter less than that of sphere 142 but sufficiently great so as to enable a portion of sphere 142 to extend therethrough and protrude distally from distal end portion 122 of shaft 120. As an alternative to open proximal throat 127, cavity 124 may define a closed proximal throat, except for a window configured to permit light energy transmission cable(s) 160 or light energy therefrom into cavity 124 to sphere 142. Distal end portion 122 of shaft 120 may be formed from two or more shaft components engaged to one another to define cavity 124 therein, or may include various other components secured to one another to define cavity 124 therebetween.

Sphere 142 is formed from a biocompatible material enabling transmission of light energy therethrough. More specifically, sphere 142 is configured to enable transmission of light energy within a tissue-treating wavelength range, e.g., a wavelength range from about 500 nm to about 2500 nm, therethrough, although other wavelength ranges may also be provided. Suitable materials for sphere 142 for this purpose include, but are not limited to sapphire, ruby, glass, crystal, combinations thereof, etc.

As noted above, energy transmission cable(s) 160 is configured to extend through cord 150 and surgical pencil 100 to interconnect the light energy surgical generator (not shown), activation switch 130, and tissue-treating portion 140 with one another. More specifically, a light energy transmission cable 160, e.g., a fiber optic cable or other suitable light energy transmission component, extends through shaft 120 to proximal throat 127, wherein light energy transmission cable 160 is proximally-spaced from sphere 142. Light energy transmission cable 160 is configured to direct light energy to sphere 142 which, in turn, focuses the light energy distally from distal end portion 122 of shaft 120 towards adjacent tissue to treat the adjacent tissue. Optics (not shown) may also be provided to facilitate the direction of light from the light energy transmission cable 160 to sphere 142. The shaft portions and/or other components of distal end portion 122 of shaft 120 are formed from material(s) with no or low light energy transmissibility to inhibit stray light energy from reaching tissue that is not intended to be treated. To this end, hoods, reflectors, and other structures (not shown) may be provided to redirect and/or confine light energy to a desired treatment area in the vicinity of sphere 142.

Referring still to FIGS. 1 and 2A, in use, surgical pencil 100 is positioned such that the portion of sphere 142 protruding distally from distal end portion 122 of shaft 120 contacts tissue to be treated, while distal end portion 122 of shaft 120 remains spaced from the tissue to be treated. Once positioned in this manner, activation switch 130 may be activated in a suitable fashion such that a desired light energy is transmitted to and focused from sphere 142 towards adjacent tissue to treat tissue. During tissue treatment, surgical pencil 100 may be moved along the surface of tissue in any direction and may change from one direction to any other direction. As surgical pencil 100 is moved in this manner, sphere 142 is rotated within cavity 124 and relative to tissue and shaft 120. Thus, sphere 142 is maintained in contact with tissue and smoothly rolls therealong regardless of the direction of movement of surgical pencil 100 or the change in direction of surgical pencil 100, and without impacting the transmission of light energy to sphere or the focusing of light energy from sphere 142 towards tissue to treat tissue. Further, light energy is advantageous in that it does not require a return pad or return electrical path and does not result in the possibility of alternative current paths.

Figure 2B:
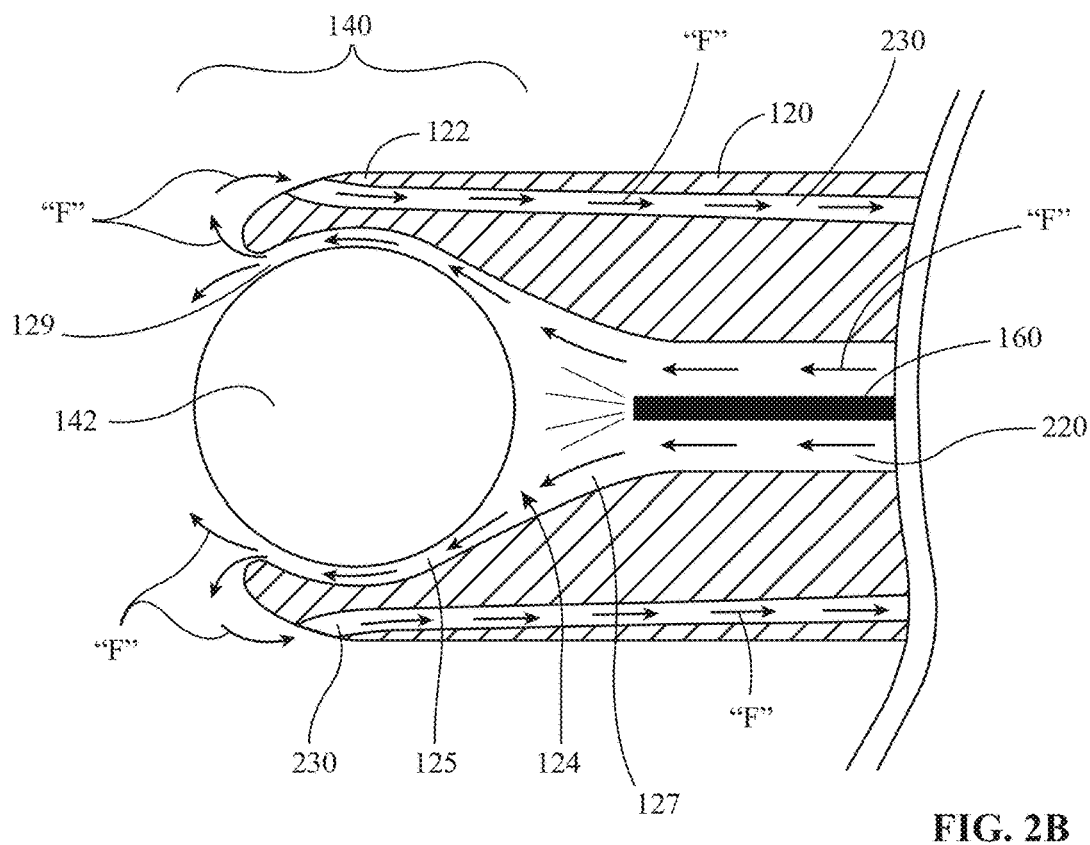
FIG. 2B is an enlarged, longitudinal, cross-sectional view of the distal end portion of another surgical pencil provided in accordance with the present disclosure, similar to the surgical pencil of FIG. 1.

Turning to FIG. 2B, in conjunction with FIG. 1, in embodiments, shaft 120 may define a fluid-delivery lumen 220 extending therethrough that is configured to direct fluid "F" between sphere 142 and the interior surface(s) of distal end portion 122 of shaft 120 that defines cavity 124. The fluid "F" may be a gas, liquid, or other suitable fluid, and may be pumped from a reservoir (not shown) disposed on or within handle 110 or from a remote reservoir (not shown) via one or more tubes extending through cord 150 or a separate cord (not shown). The pump (not shown) may likewise be disposed on or within handle 110 or remote therefrom. Fluid-delivery lumen 220, in addition to serving as a supply line for fluid "F," may also house light energy transmission cable 160, although separate lumens for the fluid "F" and light energy transmission cable 160 may alternatively be provided. The supply of fluid "F" may be initiated upon activation of activation switch 130 (simultaneously therewith, or offset before or after the initiation of energy supply) or via a separate switch (not shown).

In use, the supply of fluid "F" about sphere 142 maintains a positive pressure on sphere 142 so as to resiliently retain sphere 142 in a "floating" position, wherein sphere 142 protrudes distally from distal end portion 122 of shaft 120 despite opposing forces acting thereon from tissue in contact with sphere 142. This configuration helps maintain sphere 142 in contact with tissue as sphere 142 travels across irregular tissue surfaces, different tissue types, and other tissue features. The expulsion of fluid "F" from distal end portion 122 of shaft 120 also inhibits debris and other materials from collecting on sphere 142 and passing between sphere 142 and distal end portion 122 of shaft 120 and into cavity 124. In addition, the flow of fluid "F" helps cool tissue-treating portion 140 of surgical pencil 100 and/or surrounding tissue during tissue treatment.

Continuing with reference to FIG. 2B, in conjunction with FIG. 1, shaft 120 may further include one or more suction lumens 230 operable to connect to a pump (not shown) to suction fluid "F" from the surgical site into surgical pencil 100 and return fluid "F" to a reservoir (not shown). Fluid "F" may be pumped out of surgical pencil 100 and suctioned back into surgical pencil 100 as part of a semi-closed loop system or an open loop system. Further, a single inflow/outflow reservoir (on or within handle 100 or remote therefrom) may be utilized, or separate reservoirs (on or within handle 100 or remote therefrom) may be provided. The suction lumen 230 may be an annular lumen (as shown) defined through shaft 120 or may include separate lumens arranged in other suitable fashions within shaft 120 or within an outer sleeve (not shown) surrounding shaft 120. A separate suction device (not shown) may alternatively be utilized to withdraw fluid "F" from the surgical site.

Figure 2C:
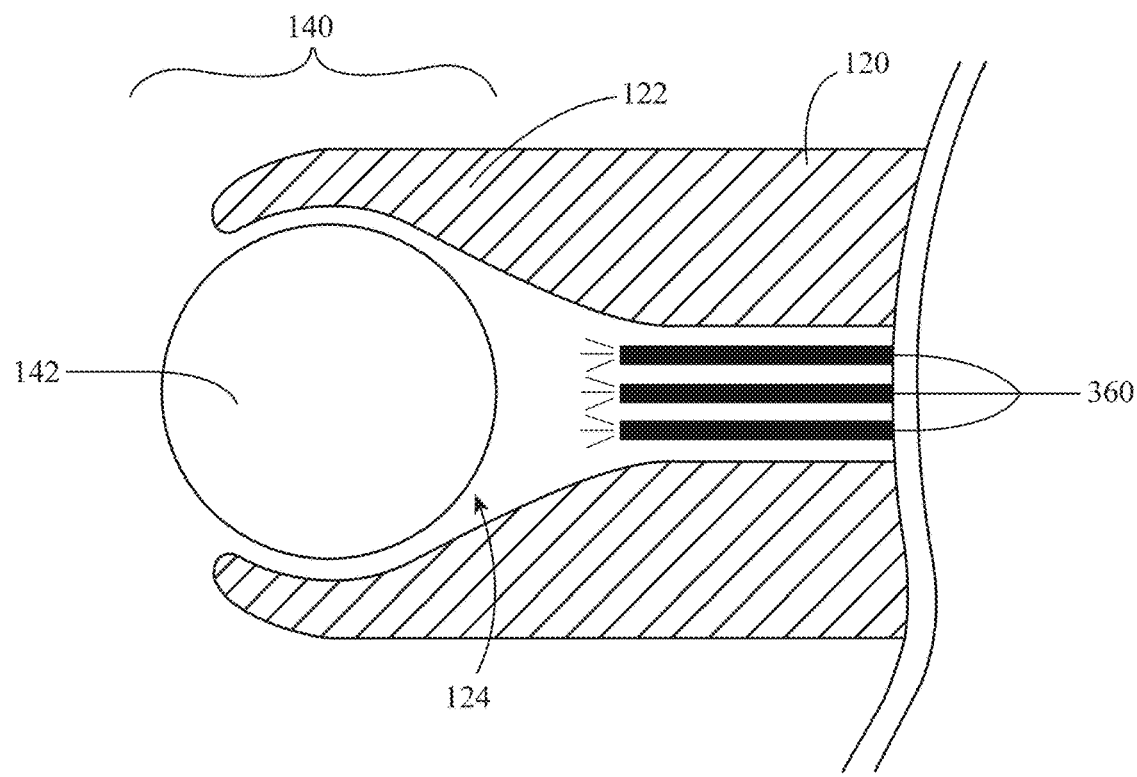
FIG. 2C is an enlarged, longitudinal, cross-sectional view of the distal end portion of another surgical pencil provided in accordance with the present disclosure, similar to the surgical pencil of FIG. 1.

Turning to FIG. 2C, in conjunction with FIG. 1, in embodiments, multiple light energy transmission cables 360 may be provided. One or more of the light energy transmission cables 360 may be configured, as detailed above, to transmit light energy to sphere 142 such that sphere 142 focuses the light energy towards tissue to treat tissue. Providing multiple light energy transmission cables 360 enables a combination of different wavelengths of light energy to be transmitted to sphere 142 and, ultimately, to tissue, to achieve a desired tissue effect.

One or more of the other light energy transmission cables 360 may serve as an optical sensor configured to sense one or more optical properties of tissue to determine tissue type, monitor tissue treatment, determine tissue temperature, determine electrical characteristics of tissue, etc. More specifically, one light energy transmission cable 360 may serve as an emitter and another light energy transmission cable 360 may collect light reflected from tissue to serve as a detector, although other configurations may also be provided. Optical tissue property information collected by one or more of the light energy transmission cables 360 may be communicated to the light energy surgical generator (not shown) to enable monitoring of tissue treatment, automatic shut off (for safety purposes and/or upon completion of tissue treatment), automatic adjustment of energy levels and/or waveforms during tissue treatment, and/or to inhibit treatment of certain tissue types. Suitable optical sensors and optical feedback mechanisms for the above purposes are disclosed in U.S. Patent Application Publication No. 2010/0296238, filed on May 16, 2011; U.S. Patent Application Publication No. 2010/0217258, filed on Jan. 30, 2008; and U.S. Patent Application Publication No. 2012/0226272, filed on Mar. 4, 2011, the entire contents of each of which are incorporated herein by reference.

Figure 2D:
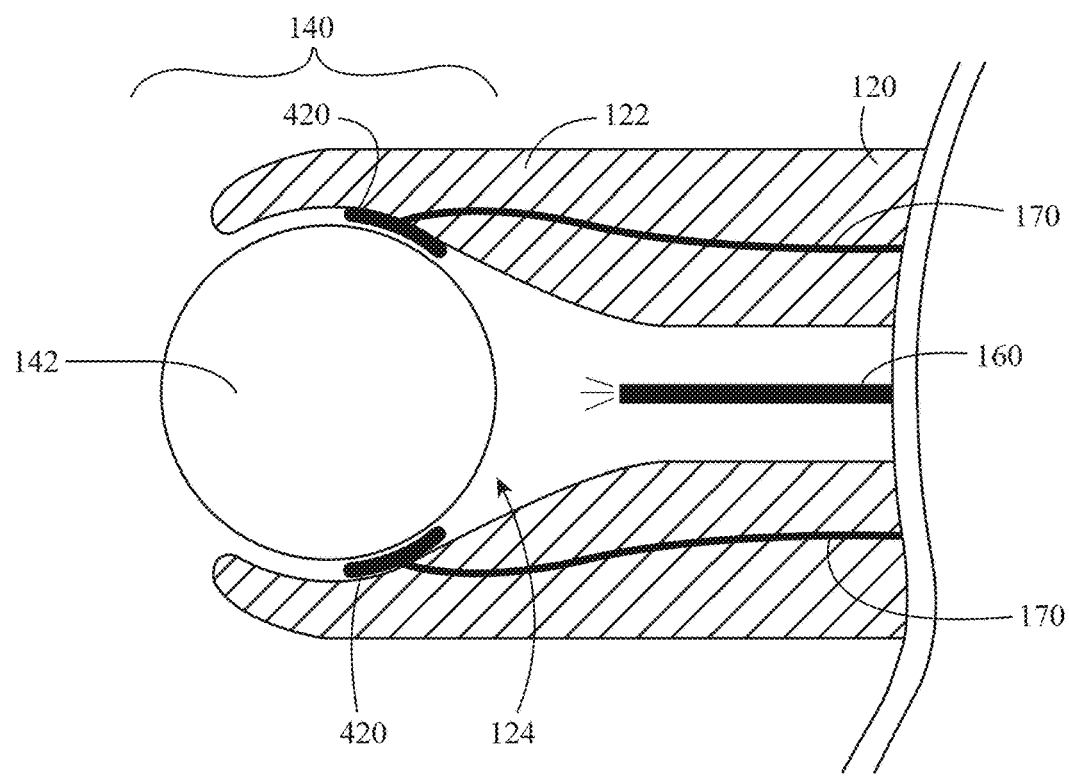
FIG. 2D is an enlarged, longitudinal, cross-sectional view of the distal end portion of another surgical pencil provided in accordance with the present disclosure, similar to the surgical pencil of FIG. 1.

Referring to FIG. 2D, in conjunction with FIG. 1, in embodiments, tissue-treating portion 140 of surgical pencil 100 includes one or more pressure sensors 420 disposed on the interior surface(s) of distal end portion 122 of shaft 120 that define cavity 124. Pressure sensors 420 are configured to sense a pressure exerted by sphere 142 against the interior surface(s) of distal end portion 122 of shaft 120 to, in turn, determine a pressure exerted by sphere 142 against tissue in contact therewith and/or a compressibility of tissue in contact with sphere 142. In this manner, surgical pencil 100 may function as a touch probe, either during tissue treatment or independently thereof. When used during tissue treatment, pressure information from pressure sensors 420 may be communicated to the light energy surgical generator (not shown) via control wires 170 to enable monitoring of tissue treatment, automatic shut off (for safety purposes and/or upon completion of tissue treatment), automatic adjustment of energy levels and/or waveforms during tissue treatment, and/or to inhibit treatment of certain tissue types. It should be understood that pressure sensors 420 will sense pressure exerted by sphere 142 against the interior surface(s) of distal end portion 122 of shaft 120 even in those embodiments (such as is shown in FIG. 2B) where fluid in interposed between sphere 142 and the interior surface(s) of distal end portion 122 of shaft 120.

Turning to FIG. 3, surgical forceps 500 generally includes a housing 510, a shaft 520 extending distally from housing 510, an end effector assembly 530 disposed at a distal end portion of shaft 520, a movable handle 540, a trigger 550, a rotation knob 560, a first activation switch 570, a second activation switch 580, and a cord 600. End effector assembly 530 includes first and second jaw members 532, 534 and a light-energy tissue-treating portion 640, as detailed below.

Movable handle 540 is operably coupled to housing 510 and movable relative to a stationary handle portion 512 of housing 510 between an initial position and a compressed position. A drive assembly (not shown) extends through housing 510 and shaft 520 and is operably coupled between movable handle 540 and first and second jaw members 532, 534 of end effector assembly 530 such that movement of movable handle 540 between the initial position and the compressed position pivots one or both of jaw members 532, 534 relative to the other between a spaced-apart position and an approximated position to grasp tissue therebetween. A suitable drive assembly for these purposes is detailed in U.S. Patent Application Pub. No. 2013/0296922 to Allen, I V et al., the entire contents of which are hereby incorporated herein by reference.

Trigger 550 is operably coupled to housing 510 and movable relative thereto between an un-actuated position and an actuated position. A knife deployment assembly (not shown) extends through housing 510 and shaft 520 and is operably coupled between trigger 550 and a knife (not shown) associated with end effector assembly 530 such that movement of trigger 550 from the un-actuated position to the actuated position advances the knife from a retracted position to an extended position, wherein the knife extends between jaw members 532, 534 to cut tissue disposed therebetween. A knife and knife deployment assembly for these purposes is detailed in U.S. Patent Application Pub. No. 2013/0296922 to Allen, I V et al., previously incorporated herein by reference in its entirety.

Rotation knob 560 is operably associated with housing 510 and extends from either side thereof to enable manual manipulation by a user. Rotation knob 560 is coupled to shaft 520 which, in turn, supports end effector assembly 530 at a distal end portion thereof. As a result, rotation of rotation knob 560 in either direction rotates shaft 520 and end effector assembly 530 relative to housing 510 in a corresponding direction.

First and second activation switches 570, 580 are disposed on housing 510, while cord 600 extends from housing 510. Cord 600 is adapted to connect to a multi-output surgical generator configured to deliver bipolar RF energy and light energy to surgical forceps 500, although cord 600 may be bifurcated (or separate cords provided) and configured to couple to two separate generators, one for RF energy and the other for light energy. Alternatively, the RF energy-generating components and power components therefor may be disposed on or within housing 510 and/or the light energy-generating components and power components therefor may be disposed on or within housing 510. As an alternative to first and second jaw members 532, 534 being configured to supply RF energy to tissue grasped therebetween, other suitable energy modalities and/or manners of treating tissue grasped between first and second jaw members 532, 534 are also contemplated, e.g., ultrasonic, light energy, microwave, cryogenic, argon plasma, etc. Further, the light-energy tissue-treatment features of the present disclosure may be incorporated into other surgical instruments including energy-based surgical instruments, e.g., ultrasonic surgical instruments, microwave surgical instruments, cryogenic surgical instruments, etc., and/or mechanical surgical instruments, e.g., graspers, shavers, clip appliers, staplers, etc.

Cord 600 includes a plurality of electrical lead wires (not shown) extending therethrough and into housing 510. The electrical lead wires (not shown) are configured to electrically couple the generator with first activation switch 570 and jaw members 532, 534 of end effector assembly 530 such that RF energy is supplied to tissue-treating plates 533, 535 of jaw members 532, 534, upon activation of activation switch 570. As such, RF energy may be conducted through tissue grasped between tissue-treating plates 533, 535 of jaw members 532, 534, respectively, to treat, e.g., seal, tissue. Second activation switch 580, similar to activation switch 130 of surgical pencil 100 (FIG. 1), is operably coupled to a light-energy transmission cable 644 and the generator to enable the selective supply of light energy to light-energy tissue-treating portion 640 for treating tissue upon activation of second activation switch 580. Second activation switch 580 may be configured similarly to any of the embodiments of activation switch 130 (FIG. 1) detailed above.

Figure 4A:
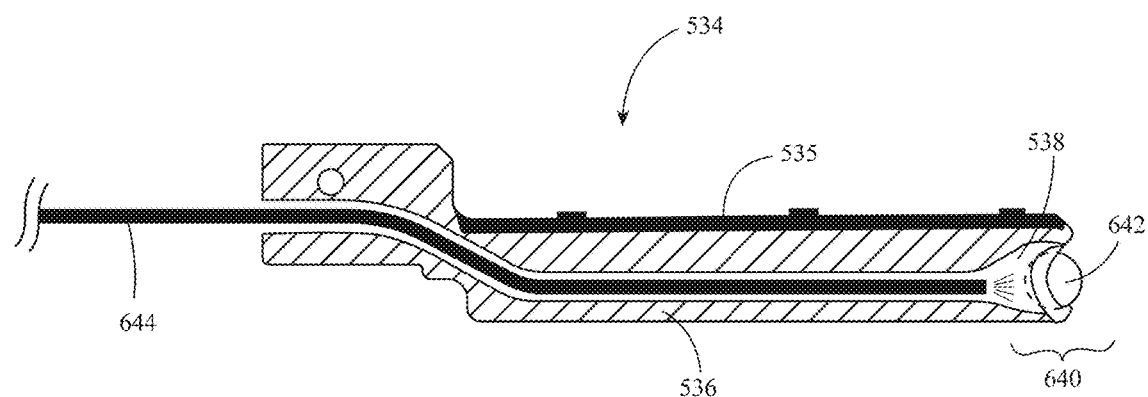
FIG. 4A is an enlarged, longitudinal, cross-sectional view of one of the jaw members of the end effector assembly of the multi-function surgical instrument of FIG. 3.

With additional reference to FIG. 4A, jaw member 534 of end effector assembly 530 of surgical forceps 500 includes light-energy tissue-treating portion 640 incorporated therein. Jaw member 534 defines a jaw housing 536 which supports tissue-treating plate 535 thereon and includes light-energy transmission cable 644 extending therethrough. Light-energy tissue-treating portion 640 includes a sphere 642 captured within a cavity 538 defined within jaw housing 536, which serves as the body of tissue-treating portion 640. Light-energy transmission cable 644 is proximally-spaced from sphere 462. Light-energy tissue-treating portion 640 may be configured similarly to any of the embodiments of light-energy tissue-treating portion 140 (FIGS. 1 and 2A-2D) detailed above. Light-energy tissue-treating portion 640 may also provide any of the functionality detailed above with respect to tissue-treating portion 140 (FIGS. 1 and 2A-2D) together with the functionality of grasping, treating, and/or cutting tissue provided by effector assembly 530, thus making surgical forceps 500 a multi-purpose surgical instrument.

Figure 4B:
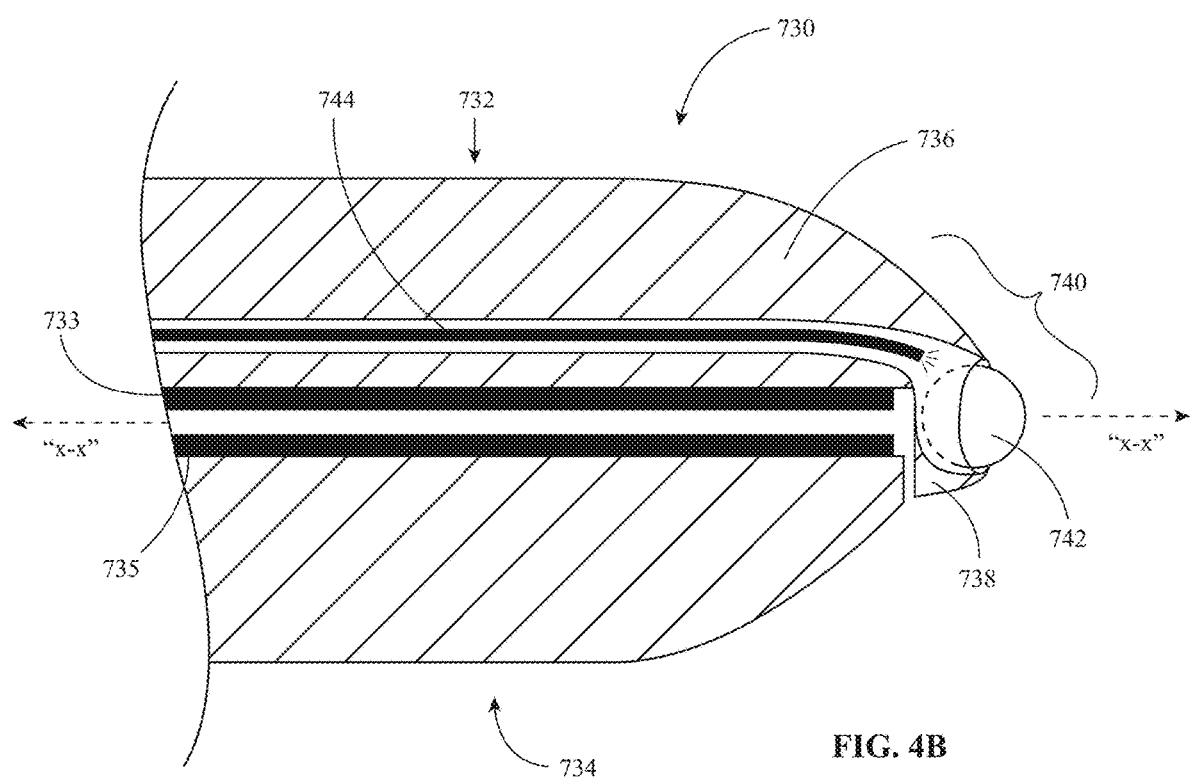
FIG. 4B is an enlarged, longitudinal, cross-sectional view of another end effector assembly configured for use with the multi-function surgical instrument of FIG. 3.

Referring to FIG. 4B, in conjunction with FIG. 3, another embodiment of an end effector assembly configured for use with surgical forceps 500 is identified by reference numeral 730. End effector assembly 730 includes jaw members 732, 734 having electrically-conductive plates 733, 735, respectively, and is configured to grasp, treat, and cut tissue, and a light-energy tissue-treating portion 740. End effector assembly 730 is similar to end effector assembly 530 (FIG. 3), but differs from end effector assembly 530 (FIGS. 3 and 4A) in that, rather than having light-energy tissue-treating portion 740 incorporated into the jaw housing of one of the jaw members, light-energy tissue-treating portion 740 is incorporated into a tooth 738 extending distally from jaw housing 736 of jaw member 732 and towards jaw member 734. More specifically, tooth 738, which serves as the body of light-energy tissue-treating portion 740, is positioned such that, with jaw members 732, 734 disposed in the approximated position, tooth 738 overlaps a portion of jaw member 734 such that sphere 742 of tissue-treating portion 740 is aligned with a longitudinal axis "X-X" of end effector assembly 730. Light-energy transmission cable 744 extends through jaw housing 736 of jaw member 732 to tooth 738, wherein light-energy transmission cable 744 is proximally-spaced from sphere 742. Light-energy tissue-treating portion 740 may be configured similarly to any of the embodiments of tissue-treating portion 140 (FIGS. 1 and 2A-2D) detailed above. Light-energy tissue-treating portion 740 also provides any of the functionality detailed above with respect to tissue-treating portion 140 (FIGS. 1 and 2A-2D) together with the functionality of grasping, treating, and/or cutting tissue provided by jaw members 732, 734 such that effector assembly 730 defines a multi-function configuration.

Figure 5:
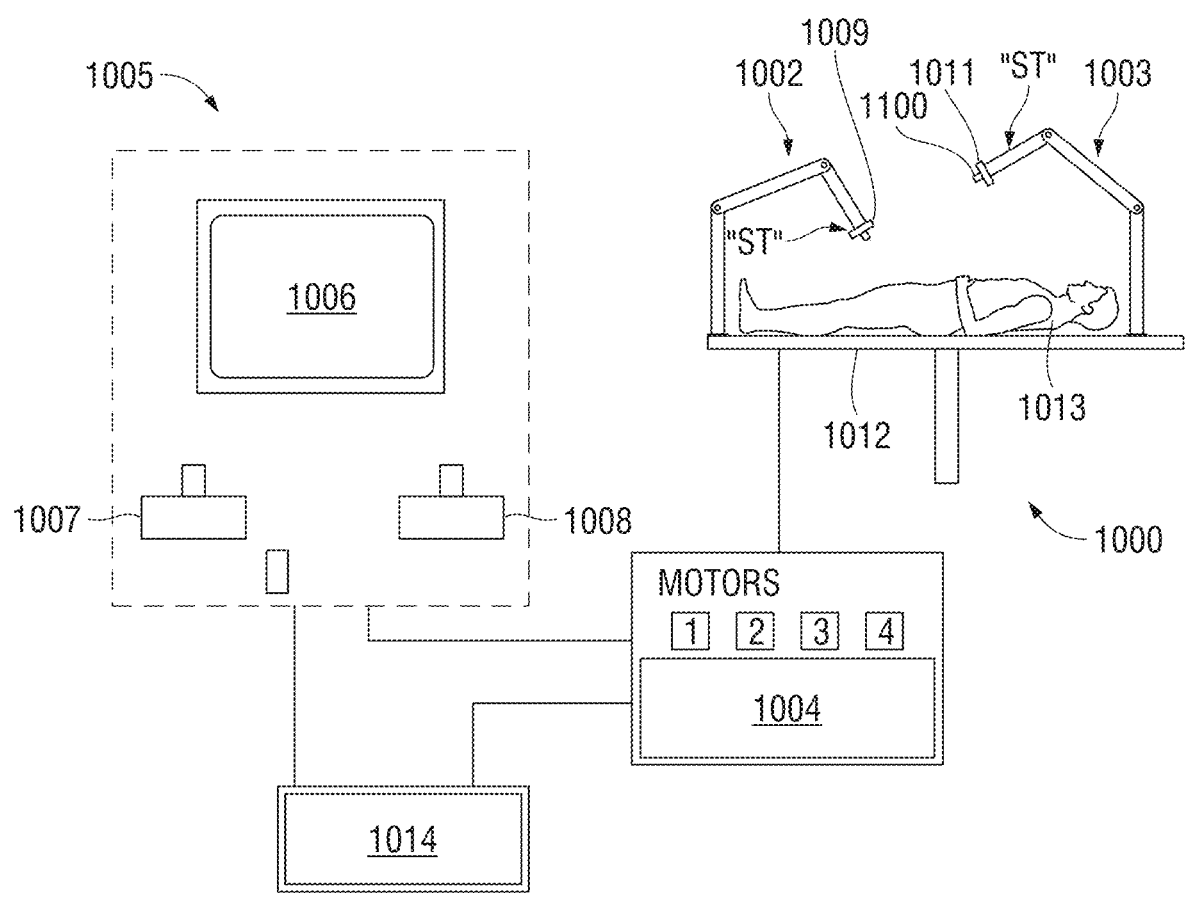
FIG. 5 is a schematic illustration of a robotic surgical system configured for use in accordance with the present disclosure.

Turning to FIG. 5, a robotic surgical system configured for use in accordance with the present disclosure is shown generally identified by reference numeral 1000. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST." One or more of the surgical tools "ST" may include a light-energy tissue-treating portion similar to those detailed above, thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a shaft;
   an end effector assembly extending distally from the shaft, the end effector assembly including:
      first and second jaw members, at least one of the first or second jaw members movable relative to the other between a spaced-apart position and an approximated position, at least one of the first or second jaw members adapted to connect to a source of energy for treating tissue grasped between the jaw members;
      a body of one of the first or second jaw members, the body defining:
         a cavity including a pocket and a distal mouth,
         a fluid-delivery lumen disposed in communication with the cavity and configured to deliver fluid to the cavity, and
         at least one suction lumen configured to permit withdrawal of the fluid;
      a light-energy transmissible sphere disposed within the cavity, the light-energy transmissible sphere captured within the pocket with a portion of the light-energy transmissible sphere extending through the distal mouth to protrude distally from the body, the light-energy transmissible sphere capable of unlimited rotation in all directions;
      at least one pressure sensor disposed within the cavity, the at least one pressure sensor configured to sense a pressure of the light-energy transmissible sphere against an interior surface of the body that defines the cavity; and
      at least one light-energy transmission cable extending through the shaft and the fluid-delivery lumen to a position proximally spaced-apart from the light-energy transmissible sphere, the at least one light-energy transmission cable configured to transmit light energy to the light-energy transmissible sphere, the light-energy transmissible sphere configured to focus the light energy towards tissue to treat tissue.

2. The surgical instrument according to claim 1, wherein the at least one light transmission cable includes:
   a first light-energy transmission cable configured to convey light of a first wavelength; and
   a second light-energy transmission cable configured to convey light of a second wavelength different from the first wavelength.

3. The surgical instrument according to claim 1, further comprising a handle and at least one fluid reservoir within the handle.

4. The surgical instrument according to claim 1, further comprising at least one wire connected to the at least one pressure sensor, the at least one wire configured to convey pressure information from the at least one pressure sensor.

5. The surgical instrument according to claim 4, wherein the at least one wire is configured to convey pressure information from the at least one pressure sensor while fluid is delivered to the cavity by the fluid-delivery lumen.

6. A surgical instrument, comprising:
   a shaft;
   an end effector assembly extending distally from the shaft, the end effector assembly including:
      first and second jaw members, at least one of the first or second jaw members movable relative to the other between a spaced-apart position and an approximated position, at least one of the first or second jaw members adapted to connect to a source of energy for treating tissue grasped between the jaw members;
      a body of one of the first or second jaw members, the body defining a cavity including a pocket and a distal mouth;
      a light-energy transmissible sphere disposed within the cavity, the light-energy transmissible sphere captured within the pocket with a portion of the light-energy transmissible sphere extending through the distal mouth to protrude distally from the body, the light-energy transmissible sphere capable of unlimited rotation in all directions;
      at least one pressure sensor disposed within the cavity, the at least one pressure sensor configured to sense a pressure of the light-energy transmissible sphere against an interior surface of the body that defines the cavity;
      and at least one light-energy transmission cable extending through the shaft to a position proximally spaced-apart from the light-energy transmissible sphere, the at least one light-energy transmission cable configured to transmit light energy to the light-energy transmissible sphere, the light-energy transmissible sphere configured to focus the light energy towards tissue to treat tissue.

7. A surgical instrument, comprising:
   a shaft;
   an end effector assembly extending distally from the shaft, the end effector assembly including:
      first and second jaw members, at least one of the first or second jaw members movable relative to the other between a spaced-apart position and an approximated position, at least one of the first or second jaw members adapted to connect to a source of energy for treating tissue grasped between the jaw members;
      a body of one of the first or second jaw members, the body defining:
         a cavity including a pocket and a distal mouth,
         a fluid-delivery lumen disposed in communication with the cavity and configured to deliver fluid to the cavity, and
         at least one suction lumen configured to permit withdrawal of the fluid;
      a light-energy transmissible sphere disposed within the cavity, the light-energy transmissible sphere captured within the pocket with a portion of the light-energy transmissible sphere extending through the distal mouth to protrude distally from the body, the light-energy transmissible sphere capable of unlimited rotation in all directions; and at least one light-energy transmission cable extending through the shaft and the fluid-delivery lumen to a position proximally spaced-apart from the light-energy transmissible sphere, the at least one light-energy transmission cable configured to transmit light energy to the light-energy transmissible sphere, the light-energy transmissible sphere configured to focus the light energy towards tissue to treat tissue.

* * * * *